(12) United States Patent
de Vos et al.

(10) Patent No.: US 6,225,463 B1
(45) Date of Patent: May 1, 2001

(54) SYNTHESIS OF NEW β-LACTAMS

(75) Inventors: Dick de Vos, Oegstgeest (NL); Stephen Brown, Lowton (GB); Allan M. Jordan, Calcot (GB); Nicholas J. Lawrence, Prestwich (GB); Alan Th. McGown, Didsbury (GB)

(73) Assignees: Pharmachemie B.V., Maarlem (NL); Cancer Research Campaign Technology Ltd., London (GB)

( * ) Notice: Subject to any disclaimer, the term of this patent is extended or adjusted under 35 U.S.C. 154(b) by 0 days.

(21) Appl. No.: 09/210,591

(22) Filed: Dec. 15, 1998

(30) Foreign Application Priority Data

Dec. 22, 1997 (EP) .................................... 97204075

(51) Int. Cl.$^7$ ................... C07D 205/08; C07D 305/14; C07B 57/00; C07C 213/10
(52) U.S. Cl. .................... 540/357; 540/354; 549/510; 549/511; 564/304; 564/389
(58) Field of Search ................... 540/354, 357; 549/510, 511; 564/304, 389

(56) References Cited

FOREIGN PATENT DOCUMENTS

| | | |
|---|---|---|
| 0 400 971 | 12/1990 | (EP) . |
| 0 552 041 | 7/1993 | (EP) . |
| 0 582 469 | 2/1994 | (EP) . |
| 0 627 418 | 12/1994 | (EP) . |
| 0 694 539 | 1/1996 | (EP) . |
| wo 96/20926 | 7/1996 | (WO) . |

OTHER PUBLICATIONS

J.D. Bourzat et al., "A practical access to chiral phenylisoserinates, preparation of taxotere analogs.", Tetrahedron Letters, vol. 34, No. 38, 1993, Oxford, GB, pp. 6049–6052, XP0020644288.

I. Ojima et al., "New and efficient approaches to the semi-synthesis of taxol and its C–13 side chain analogs by means of beta–lactam synthon method.", Tetrahedron, vol. 48, No. 34, 1992, Oxford, GB, pp. 6985–7012, XP000561212.

Hart, D.J. et al., "Preparation of primary amines and 2–azetidinones via N–trimethylsilylimines.", Journal of Organic Chemistry, vol. 48, No. 3, 1983, Easton, US, pp. 289–294, XP002064429.

Farina, V. et al., "A simple chiral synthesis fo the taxol side chain.", Synlett, No. 9, 1992, pp. 761–763, XP002064430.

*Primary Examiner*—Ba K. Trinh
(74) *Attorney, Agent, or Firm*—Browdy And Neimark

(57) ABSTRACT

The object of the present invention is the development of new chiral auxiliaries for improved β-lactam formation that control both the diastereoselectivity of β-lactam formation and which can be removed without destruction of the sensitive azetidinone ring, providing valuable intermediates for coupling to the C-13 hydroxyl group of anti-tumor taxanes, such as paclitaxel. Further, the object of the present invention is enantiomerically pure (S)-(–)-1-(p-methoxyphenyl)propyl-1-amine.

9 Claims, No Drawings

SYNTHESIS OF NEW β-LACTAMS

BACKGROUND OF THE INVENTION

The present invention is directed to a novel process for the convenient preparation of β-lactams which can be used for the preparation β-lactams which serve as precursors of the paclitaxel side-chain.

Paclitaxel (Taxol™), isolated in minute quantities from the bark of the pacific yew *Taxus brevifolia*, is a potent anticancer agent used clinically to treat advanced ovarian and breast cancers. Paclitaxel is a member of the taxane natural products having the following structure:

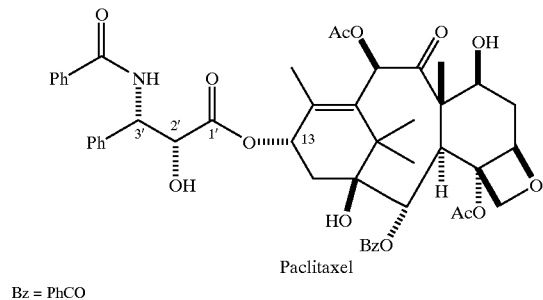

Paclitaxel
Bz = PhCO

The difficulties in meeting the growing demand for large quantities of paclitaxel has been circumvented by its semi-synthesis from 10-deacetylbaccatin-III, a taxane isolated from the needles of the English yew *Taxus baccata*. The structure of 10-deacetylbaccatin-III is shown below:

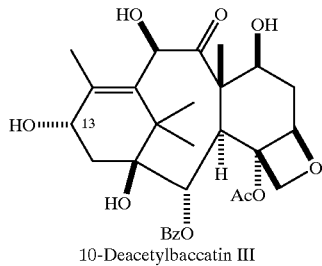

10-Deacetylbaccatin III
Bz = PhCO

Semi-synthetic paclitaxel is made from derivatives of 10-deacetylbaccatin-III by coupling a suitable side chain precursor to the free hydroxyl group at position 13. In addition all the total syntheses reported to date the side-chain has been installed in a similar way as one of the late steps.[1] The current interest in paclitaxel has therefore created a need for good synthetic routes to such precursors of the C-13 side chain. The side-chain is also a very important structural feature that is, in part, responsible for paclitaxel's impressive ability to stabilise microtubules. As a consequence, many analogues of paclitaxel possessing a modified C-13 side chain have been made by semi-synthesis.

Of the numerous synthetic routes to the side-chain, β-lactams constitute one of the most important type of side-chain precursor and can be made via the Staudinger reaction between an imine and a ketone.[2] The β-lactam 3 has previously been made by the Staudinger reaction between the imine 1 and the ketene derived in situ from acetoxyacetyl chloride 2 (3:4, 75:25, 74%).[3] However, the β-lactam was ring-opened in the next step of what constituted a synthesis of the phenylisoserine side-chain: the auxiliary was removed by hydrogenolysis.

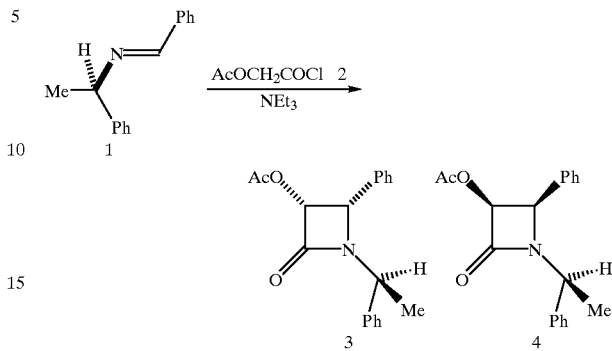

Farina and co-workers have also used a similar chiral auxiliary based approach to the synthesis of the C-13 side chain.[4] They used a derivative of L-threonine as the auxiliary, as shown below. Although the diastereoselectivity of β-lactam formation is good (10:1), four reactions are required to remove the auxiliary via treatment with fluoride ion, methanesulfonyl chloride and triethylamine, ozone, and sodium bicarbonate in 66% overall yield. These steps necessarily increase the costs of a process and severely limit the number of possible compatible functional groups present in any side chain analogue. Additionally, the L-threonine derivative is not commercially available and would be expensive to make.

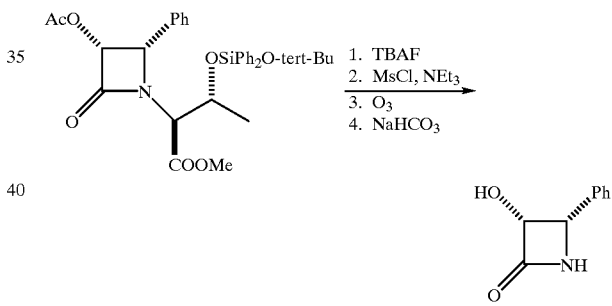

TBAF : tetrabutylammonium fluoride
MsCl : methanesulfonyl chloride

A new auxiliary to control the diastereoselectivity in the ringforming reaction which could be made inexpensively and also be removed without destruction of the β-lactam ring in a single step is therefore needed. This could be obtained by the use of p-methoxyphenyl substituted amines. We have now developed a new stereocontrolled route to the paclitaxel β-lactam side-chain precursor using a chiral auxiliary that is cleaved oxidatively from the lactam nitrogen atom.

SUMMARY OF THE INVENTION

The object of the present invention is the development of new chiral auxiliaries for improved β-lactam formation that control both the diastereoselectivity of β-lactam formation and which can be removed without destruction of the sensitive azetidinone ring, providing valuable intermediates for coupling to the C-13 hydroxyl group of anti-tumor taxanes.

The present invention is therefore directed to a process of preparing a β-lactam of formula 9

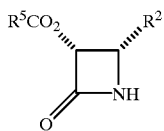
(9)

wherein $R^2$ is aryl, substituted aryl, $C_1$–$C_5$ alkyl, $C_1$–$C_5$ alkenyl or $C_1$–$C_5$ alkynyl, and $R^5$ is aryl, substituted aryl or $C_1$–$C_5$ alkyl, comprising the steps of:

a) reaction of an S-amine of formula 5

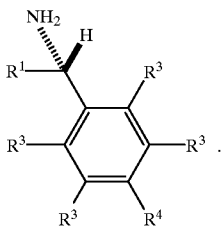

wherein
$R^1$ is $C_1$–$C_5$ alkyl,
$R^3$ is hydrogen, $C_1$–$C_5$ alkyl, $C_1$–$C_5$ alkoxyl or aryloxy, and
$R^4$ is $C_1$–$C_5$ alkoxyl or aryloxy, with a aldehyde of formula $R^2$CHO, wherein $R^2$ is as defined above;
to obtain a compound of formula 6

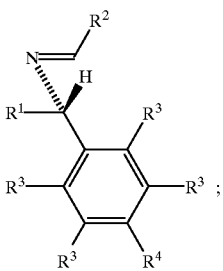

wherein $R^1$, $R^2$, $R^3$ and $R^4$ are as defined above, b) reaction of the compound of formula 6 with an acyl-chloride $R^5CO_2CH_2COCl$ of formula 7, wherein $R^5$ is as defined above, in the presence of triethylamine, to obtain a mixture of diastereo-isomeric β-lactams of the formulae 8a and 8b:

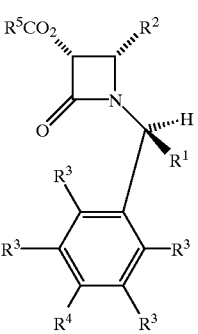
(8a)

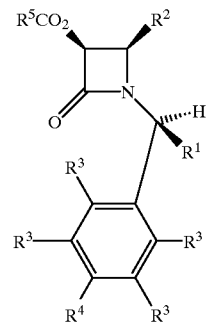
(8b)

wherein $R^1$, $R^2$, $R^3$, $R^4$ and $R^5$ are as defined above, and c) separation of the β-lactams of formulae 8a and 8b, to obtain an enantiomerically pure β-lactam of formula 8a, followed by treatment of said β-lactam of formula 8a with cerium ammonium nitrate $[Ce(NH_4)_2(NO_3)_6]$ in the presence of acetonitrile and water, to obtain the β-lactam having formula 9.

According to the above process, the required diastereoisomer (−)-8a could be isolated free of the isomer 8b in a high yield.

Expediently, the β-lactams of formulae 8a and 8b are separated by recrystallisation from an ethyl acetate/hexane mixture.

Preferably, the abovementioned step (b) of the process according to the invention is effected in hexane, benzene or in DMF, for the selectivity of the β-lactams (±)-8a and (±)-8b appeared to be somewhat dependent upon the reaction solvent, as will be explained below.

Expediently, compounds are used in the present process wherein
$R^1$ is $C_1$–$C_5$ alkyl,
$R^2$ is aryl, substituted or not,
$R^3$ is hydrogen,
$R^4$ is $C_1$–$C_5$ alkoxyl or aryloxy, and
$R^5$ is $C_1$–$C_5$ alkyl.

A further object of the present invention is enantiomerically pure (S)-(−)-1-(p-methoxy-phenyl)propyl-1-amine. This compound could be prepared in a 89% overall yield by the sodium/ethanol reduction of the oxime p-methoxypropiophenone.

The enantiomerically pure chiral auxiliary S-(−)-1-(p-methoxyphenyl)-propyl-1-amine is required for the production of a single diastereoisomer of paclitaxel upon coupling with 10-deacetylbaccatin-III, and represents thus a valuable intermediate in a production process of paclitaxel.

The use of this invention for the synthesis of a β-lactam, used previously as a precursor to the side chain of paclitaxel is exemplified below.

The diastereomeric β-lactams (±)-11 and (±)-12 were prepared by the Staudinger reaction between the imine (±)-10 [derived from 1-(p-methoxyphenyl)propyl-1-amine; see below] and acetoxyacetyl chloride 2 in the usual way. The selectivity was somewhat dependent upon the reaction solvent; in hexane, (±)-11:(±)-12 67:33, 54%, in benzene, (±)-11: (±)-12 74:26, 78%; and in DMF (±)-11:(±)-12 70:30, 85%. When the mixture of (±)-11 and (±)-12 was treated with ceric ammonium nitrate in a mixture of water and acetonitrile (3:5) for 1 h at 0° C. the reaction proceeded cleanly to give the azetidinone (±)-13 (85%) and p-methoxypropiophenone. This is therefore a key feature of the invention as the auxiliary group is easily removed to reveal the β-lactam intact.

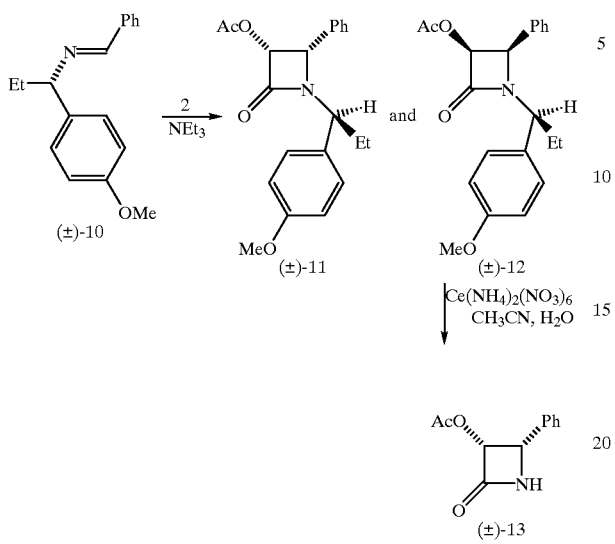

The preparation of the enantiomerically pure β-lactam is possible by the use of an enantiomerically pure chiral auxiliary.

The preparation of enantiomerically pure (S)-(−)-1-(p-methoxyphenyl)propyl-1-amine (−)-14 is achieved by resolution of its salt with N-acetyl-L-leucine 15. The 1-(p-methoxyphenyl)propyl-1-amine (±)-14 is in turn prepared in 89% overall yield by the sodium/ethanol reduction of the oxime p-methoxypropiophenone. Reaction of the amine with N-acetyl-L-leucine 15 gave the expected diastereoisomeric salts. The less soluble (S)-amine N-acetyl-L-leucine salt 16 was obtained (30%) by fractional crystallisation of the mixture from water. Treatment of the salt 16 with sodium hyroxide solution gave the amine (S)-(−)-1-(p-methoxyphenyl)propyl-1-amine (−)-14 (quant.) and recovered N-acetyl-L-leucine 15 (88%).

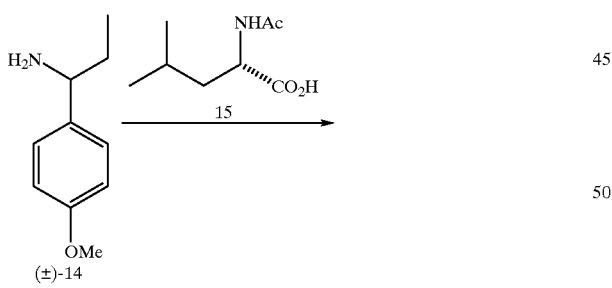

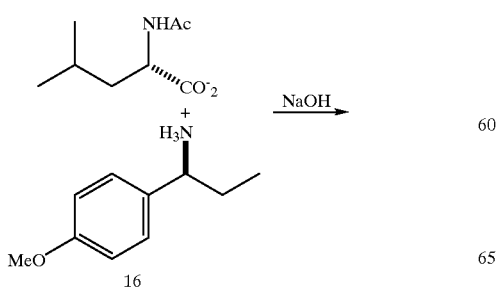

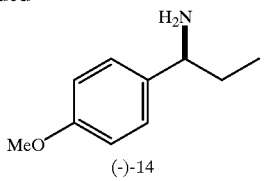

The imine (S)-(−)-10 [quantitatively obtained from (S)-(−)-14] gave a 73:27 mixture (78%) of enantiomerically pure (−)-11 and 12 upon reaction with acetoxyacetyl chloride 2. Fortunately the required major diastereoisomer (−)-11 could be isolated free of 12 by recrystallisation from ethyl acetate/hexane [52% from (S)-10]. Treatment of the now pure (−)-11 with ceric ammonium nitrate gave the known azetidinone (−)-13. We were able to isolate the by-product p-methoxypropiophenone in 77% yield, which in principle can be recycled in the synthesis of further (S)-(−)-(p-methoxyphenyl)propyl-1-amine.

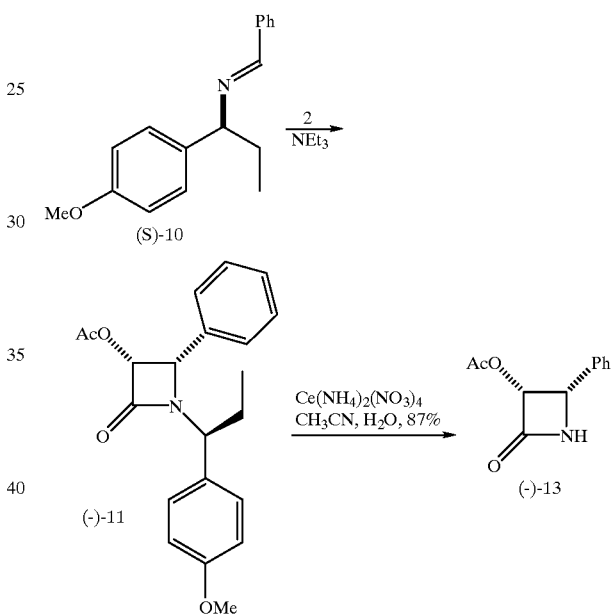

The invention will be explained further in the following examples.

EXAMPLE 1

Preparation of the Oxime of P-methoxypropiophenone

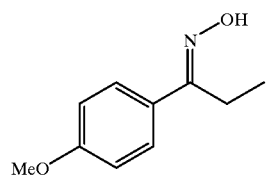

4-Methoxypropiophenone (100 g, 0.61 mol) and hydroxylamine hydrochloride (61 g, 0.88 mol) were dissolved in ethanol (375 cm$^3$) and water (120 cm$^3$). This solution was added to a solution of potassium hydroxide (93 g, 1.65 mol)

in water (95 cm³) and the resultant mixture refluxed for 2.5 hours. After addition of water (1200 cm³) and cooling, the pH of the solution was adjusted to 7 with aqueous hydrochloric acid (1 M). The solution was extracted with chloroform (3×500 cm³) and the organic extracts dried (magnesium sulfate), filtered and concentrated in vacuo to give the oxime as a white powder (109 g, 100%) which was used without purification in the next stage; m.p. 63–64 C.; $v_{max}$ (KBr Disc)/cm⁻¹ 3281, 3235, 3127, 3071, 2965, 2935, 1606, 1513, 1462, 1300, 1252, 1241, 1181, 1034, 1026, 971, 910, 837, 831, 597; δ ¹H (300 MHz, CDCl₃) 1.16 (3H, t, J 7.6 Hz, 3-H), 2.79 (2H, q, J 7.6 Hz, 2-H), 3.83 (3H, s, OMe), 6.90 (2H, d, J 8.9 Hz, 3'-H), 7.56 (2H, d, J 8.9 Hz, 2'-H), 7.99 (1H, br s, OH), δ ¹³C (75 MHz, CDCl₃) 10.9 (CH₃); 19.6 (CH₂), 55.1 (CH₃), 113.9 (CH), 127.6 (CH), 129.7 (C), 160.1 (Cq), 160.4 (C); (CI: Found: [M]⁺ 179.0948. C₁₀H₁₃NO₂ requires 179.0946 m/z (CI) 180 ([M+H]⁺, 100%), 164 (30).

Preparation of Racemic Amine (±)-14

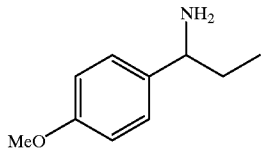

p-Methoxypropiophenone oxime (109 g, 0.61 mol) was dissolved in ethanol (600 cm³) and the solution heated to reflux. Under a nitrogen blanket, sodium metal (120 g, 5.2 mol was added in small pieces over 90 minutes. After a further 2.5 hours heating at reflux, additional ethanol (800 cm³) was slowly added over 30 minutes, followed by the slow addition of aqueous ethanol (10% water, v/v, 400 cm³) until all the sodium metal residues had been destroyed. Most of the ethanol was evaporated and then water (400 cm³) was added. Extraction of the mixture with diethyl ether (3×350 cm³), drying (magnesium sulfate) and concentration in vacuo gave a crude product, which was further purified by distillation under reduced pressure to give the amine as a colourless oil (81.7 g, 81%); b.p. 107–108° C. (5 mm Hg); $v_{max}$ (thin film on CsI plates)/cm⁻¹ 2962, 2931, 1612, 1513, 1302, 1248, 1176, 1037, 832; δ ¹H (300 MHz, CDCl₃) 0.81 (3H, t, J 7.3 Hz, 3-H), 1.60 (2H, dq, J 6.9 Hz, 7.3 Hz, 2-H), 3.71 (1H, t, J 6.9 Hz, 1-H), 3.74 (3H, s, OMe), 6.82 (2H, d, J 8.6 Hz, 3'-H), 7.18 (2H, d, J 8.6 Hz, 2'-H); m/z (FAB) 166 ([M+H]⁺, 80%), 149 (70), 136 (100).

Preparation of Racemic Imine (±)-10

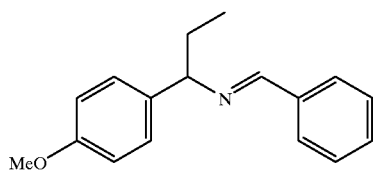

Benzaldehyde (0.67 g, 6.31 mmol) and the amine (±)-14 (0.80 g, 4.85 mmol) were stirred in dry dichloromethane (15 cm³) in the presence of 4 Å molecular sieves, at room temperature overnight, under a nitrogen atmosphere. Filtration and concentration in vacuo gave the imine (±)-10 as a yellow oil (1.09 g, 90%) which was used in the next stage without purification: $v_{max}$ (thin film on CsI plates)/cm⁻¹ 2964, 2933, 2873, 1644, 1612, 1582, 1512, 1464, 1452, 1379, 1303, 1247, 1174, 1037, 832, 694; δ ¹H (300 MHz, CDCl₃) 0.87 (3H, t, J 7.3 Hz, 3-H), 1.93 (2H, m, 2-H), 3.79 (3H, s, OMe), 4.14 (1H, t, J 6.9 Hz, 1-H), 6.88 (2H, d, J 4.6 Hz, 3'-H), 7.35 (2H, d, J 4.6 Hz, 2'-H), 7.40 (3H, m, 4"-H and 5"-H), 7.78 (2H, 3"-H), 8.31 (1H, s, 1"-H); m/z (FAB) 254 ([M+H]⁺, 80%), 224 (40), 149 (90), 121 (55).

Preparation of β-lactams (±)-11 and (±)-12

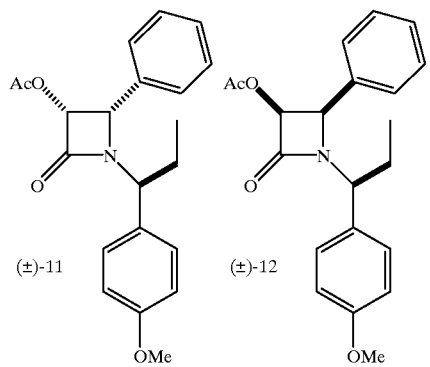

The azetidinones were prepared using the general procedure developed by Holton (EP-A-0 400 971). The imine (±)-10 (0.10 g, 0.395 mmol) and triethylamine (0.16 g, 1.68 mmol) in dry dichloromethane (1 cm³) were slowly added acetoxyacetyl chloride (53.9 mg, 0.395 mmol) in dry dichloromethane (1 cm³) at 0° C. The mixture was stirred at 0° C. for 1.5 h and then at room temperature for a further 3 h. The solution was poured into dichloromethane (10 cm³, and washed successively with hydrochloric acid (1 M, 2×5 cm³), water (5 cm³) and saturated sodium bicarbonate solution (5 cm³). The organic extract was dried (magnesium sulfate), filtered and evaporated in vacuo to give the azetidinones [78 mg, 56%; (±)-11:(±)-12 67:33] as cream powders: $v_{max}$ (K Br Disc)/cm⁻¹ 2971, 2933, 1754, 1514, 1369, 1226, 1181, 1035, 702; δ ¹H (300 MHz, CDCl₃) 0.84 (3H, t, J 7.2 Hz, major 3'-H), 0.86 (3H, t, J 7.2 Hz, minor 3'-H), 1.64 (3H, s, minor Ac), 1.66 (3H, s, major Ac), 1.85 (2H, m, major 2'-H), 2.05 (2H, m, minor 2'-H), 3.78 (3H, s, minor OMe), 3.80 (3H, s, major OMe), 4.01 (1H, t, J 9.3 Hz, minor 1'-H), 4.57 (1H, m, major 3-H), 4.60 (1H, m, minor 3-H), 4.62 (1H, t, J 9.3 Hz, major 1'-H), 5.62 (1H, d, J 4.8 Hz, major 4-H), 5.66 (1H, d, J 4.8 Hz, minor 4-H), 6.77 (2H, d, J 8.2 Hz, minor 3"-H), 6.83 (2H, d, J 8.2 Hz, major 3"-H), 7.03 (2H, d, J 8.2 Hz, minor 2"-H), 7.08 (2H, d, J 8.2 Hz, major 2"-H), 7.27 (10 H, m, Ar); m/z (FAB) 376 ([M+Na]⁺, 10%), 354 ([M+H]⁺, 50), 307 (20), 149 (100).

Preparation of Racemic β-Lactam (±)-13

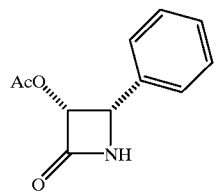

The azetidinones (±)-11 and (±)-12 (0.01 g, 0.28 mmol) were dissolved in acetonitrile (3 cm³), cooled to 0° C. and slowly added to a cooled (0° C.) solution of ceric ammonium nitrate (0.46 g, 0.85 mmol) in distilled water (5 cm³). After stirring at 0° C. for one hour, the mixture was then diluted with distilled water (15 cm³), and extracted with ethyl acetate (3×15 cm³). The organic extracts were washed with saturated sodium bicarbonate solution (10 cm³). These aqueous washings extracted with ethyl acetate (15 cm³). The combined organic phases were washed with sodium sulfite solution (10% w/v) until the aqueous layer remained colourless, then with saturated sodium bicarbonate solution (10 cm³), and brine (10 cm³). Drying (magnesium sulfate), filtration and concentration in vacuo, followed by recrystallisation from acetone and hexane gave the azetidinone (±)-13 as white crystals (0.05 g, 85%); m.p. 150–151° C.; Found C, 64.5; H, 5.1; N, 6.7. $C_{11}H_{11}NO_3$ requires C, 64.4; H, 5.4; N, 6.8%; $R_f$ 0.59 (silica, ethyl acetate); $\nu_{max}$ (KBr disc)/cm⁻¹ 3200, 1755, 1720, 1500, 1460, 1370, 1225, 1210, 1165, 1125, 820, 760, 700, 500; δ ¹H (300 MHz, CDCl₃) 1.56 (3H, s, Ac), 4.92 (1H, d, J 4.6 Hz, 3-H), 5.75 (1H, dd, J 4.6 Hz, 2.6 Hz, 4-H), 6.75 (1H, br s, NH), 7.21 (5H, m, Ph): δ ¹³C (75 MHz, CDCl₃) 19.7 (CH), 57.8 (CH), 78.1 (CH₃), 127.4 (CH), 128.2 (CH), 128.5 (CH), 134.4 (C), 165.7 (C), 169.1 (C); m/z (FAB) 206 ([M+H]⁺, 40%), 165 (60), 160 (70), 152 (90), 128 (40), 115 (45), 106 (100), 89 (75).

Preparation of Enantiomerically Pure Amine (−)-14

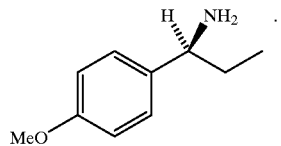

The amine (±)-14 (40 g, 0.25 mmol) and N-acetyl-(L)-leucine (44 g, 0.25 mol) in water (ca. 1600 cm³) were heated until dissolution occurred. Upon cooling to ambient temperature, the amine salt precipitated as white crystals, which were filtered from the mother liquors and washed well with water. A second recyrstallisation from water (ca. 600 cm³) gave the salt as translucent needles. These were filtered, washed well with cold water and added with stirring to sodium hydroxide solution (5 M, 200 cm³). Extraction with diethyl ether (3×150 cm³), drying (magnesium, sulfate), filtration and concentration in vacuo gave the (S)-amine (−)-14 as a colourless oil [11.8 g, 30%, 99% e.e. by chiral G.C. (see below)]: b.p. 107–108° C. (5 mm Hg); $[α]_D^{20}$ −1.25 (c 4.0, methanol); $\nu_{max}$ (thin film on CsI plates)/cm⁻¹ 2964, 2933, 2873, 1644, 1612, 1582, 1512, 1464, 1452, 1379, 1303, 1247, 1174, 1037, 832, 694; δ ¹H (300 MHz, CDCl₃) 0.81 (3H, t, J 7.3 Hz, 3-H), 1.60 (2H, dq, J 6.9 Hz and 7.3 Hz, 2-H) 3.71 (1H, t, J 6.9 Hz, 1-H), 3.74 (3H, s, OMe), 6.82 (2H, d, J 8.6 Hz, 2'-H), 7.18 (2H, d, J 8.6 Hz, 3'-H): δ ¹³C (75 MHz, CDCl₃) 10.9 (CH₃), 32.5 (CH₂), 55.1 (CH), 57.1 (CH₃), 113.6 (CH), 127.3 (CH), 138.6 (C), 158.4 (C); (EI: found: [M]⁺ 165.1158. $C_{10}H_{15}NO$ requires [M]⁺ 165.1154): m/z (FAB) 166 ([M+H]⁺, 80%), 149 (70), 136 (100). The enantiomers of the N-trifluoroacetyl derivative of 14 were clearly resolved by G.C. using a Chiraldex trifluoroacetyl-γ-cyclodextrin column. The N-trifluoroacetyl derivative of (R)-14 was 24.4 minutes whilst that of the (S)-14 derivative was 24.9 minutes [temperature 120→160° C. at 2° C. minute⁻¹ and 10 minutes at 160° C.].

Preparation of Enantiomerically Pure Imine (+)-10

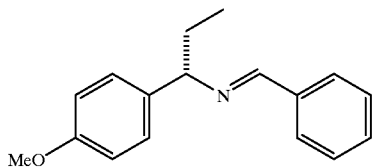

The amine (−)-14 (8.0 g, 7.0 cm³, 48.5 mmol) and benzaldehyde (5.17 g, 4.95 cm³, 48.5 mmol) were dissolved in toluene (100 cm³) with a catalytic amount of Amerlyst 15 resin (H⁺ form) and heated to reflux in a flask equipped with Dean-Stark apparatus. After two hours, the solution was filtered and concentrated in vacuo to give the imine (+)-10 as a pale brown oil (12.3 g, 100%); $[α]_D^{20}$ +37.2° (c 0.4, chloroform): $\nu_{max}$ (KBr Disc)/cm⁻¹ 2964, 2933, 2873, 1644, 1612, 1582, 1512, 1464, 1452, 1379, 1303, 1247, 1174, 1037, 832, 694: δ ¹H (300 MHz, CDCl₃) 0.87 (3H, t, J 7.3 Hz, 3-H), 1.93 (2H, m, 2-H), 3.79 (3H, s, OMe), 4.14 (1H, t, J 6.9 Hz, 1-H), 6.88 (2H, d, J 4.6 Hz, 3'-H), 7.35 (2H, d, J 4.6 Hz, 2'-H), 7.40 (3H, m, 4"-H and 5"-H), 7.78 (2H, m, 3"-H), 8.31 (1H, s, 1"-H): δ ¹³C (75 MHz, CDCl₃) 11.2 (CH₃), 31.6 (CH₂), 55.3 (CH), 76.5 (CH₃), 113.8 (CH), 128.1 (CH), 128.3 (CH), 128.5 (CH), 130.5 (CH₃), 136.5 (C), 136.7 (C), 158.5 (C), 159.5 (CH); (EI: found: [M]⁺ 253.1463. $C_{17}H_{18}NO$ requires 253.1466); m/z (FAB) 254 ([M+H]⁺, 80%), 224 (40), 149 (90), 121 (55), 91 (100).

Preparation of Enantiomerically Pure β-Lactam (−)-11

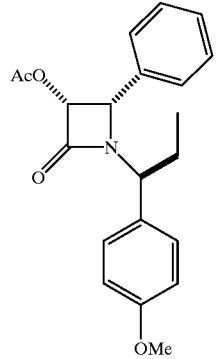

To a cold (0° C.) stirred solution of the imine (+)-10 (9.00 g, 35.5 mmol) and triethylamine (5.40 g, 7.44 cm³, 53.4 mmol) in dry benzene (120 cm³) was added acetoxyacetyl chloride (4.86 g, 3.83 cm³, 35.6 mmol) and the solution stirred at 0° C. for one hour, then at ambient temperature overnight. After this time, dichloromethane (200 cm³) was added and the solution washed with hydrochloric acid (1 M, 2×65 cm³), saturated sodium bicarbonate solution (2×50 cm³) and water (2×50 cm³). The organic fraction was dried (magnesium sulfate) filtered and concentrated in vacuo to give the azetidinone as a 2.7:1 ratio of diastereoisomers (9.9 g, 78%). Recrystallisation from ethyl acetate/hexane gave the β-lactam (−)-11 as white rod-shaped crystals (6.5 g, 52%): m.p. 117–8° C.; Found C, 71.4; H, 6.7; N, 3.9. $C_{21}H_{23}NO_4$ requires C, 71.3; H, 6.6; N, 3.9%; $[α]_D^{20}$ −11.8° (c 0.3, chloroform): $\nu_{max}$ (KBr Disc)/cm⁻¹ 2971, 2933, 1754, 1514, 1369, 1226, 1181, 1035, 702: δ ¹H (300 MHz, CDCl₃) 0.84 (3H, t, J 7.2 Hz, 3'-H), 1.66 (3H, s, Ac), 1.85

(2H, m, 2'-H), 3.80 (3H, s, OMe), 4.57 (1H, d, J 4.8 Hz, 3-H), 4.62 (1H, t, J 9.3 Hz, 1'-H), 5.62 (1H, d, J 4.8 Hz, 4-H), 6.83 (2H, d, J 8.2 Hz, 3"-H), 7.03 7.08 (2H, d, J 8.2 Hz, 2"-H), 7.27 (5 H, m, Ar): δ $^{13}$C (75 MHz, CDCl$_3$) 7.7 (CH$_3$), 11.2 (CH), 26.5 (CH$_2$), 55.3 (CH$_3$), 59.3 (CH), 61.4 (CH), 76.2 (CH), 114.1 (CH), 128.0 (CH), 128.7 (CH), 128.8 (CH), 129.2 (CH), 129.7 (C), 134.0 (C), 159.2 (C), 164.9 (C), 169.1 (C); (CI: found: [M+H]$^+$ 354.1708. C$_{21}$H$_{23}$NO$_4$ requires 354.1705): m/z (FAB) 376 ([M+Na]$^+$, 10%), 354 ([M+H]$^+$, 50), 307 (20), 149 (100).

Preparation of Enantiomerically Pure β-Lactam (−)-13

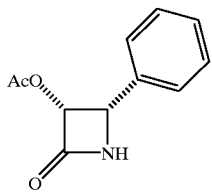

The azetidinone was prepared in a similar manner to the synthesis of (±)-13, using the azetidinone (−)-11 (6.4 g, 18.1 mmol) with other reagents scaled accordingly. Recrystallisation from ethyl acetate/hexane gave the azetidinone (−)-13 as a white powder (3.24 g, 87%) with identical spectroscopic properties to (±)-13; m.p. 151–52° C.; [α]$_D^{20}$ −45.7° (c 0.4, chloroform).

References

1 Ojima, I.; Habus, I.; Zhao, M.; Zucco, M.; Park, Y. H.; Sun, C. M.; Brigaud, T. *Tetrahedron.*, 1992, 48, 6985–7012.
2 R. A. Holton, European patent application, 1990, EP 0 400 971 A2.
3 Bourzat, J. D.; Commerçon, A. *Tetrahedron Lett.*, 1993, 34, 6049–6052.
4 Farina, V.; Hauck, S. I.; Walker, D. G. *Synlett*, 1992, 761–763.

What is claimed is:

1. A process of preparation a β-lactam of formula 9

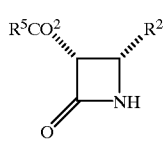

(9)

wherein R$^2$ is aryl, substituted aryl, C$_1$–C$_5$ alkyl, C$_1$–C$_5$ alkenyl or C$_1$–C$_5$ alkynyl, and R$^5$ is aryl, substituted aryl or C$_1$–C$_5$ alkyl, comprising the steps of:

a) reaction of an S-amine of formula 5

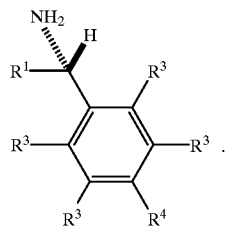

wherein
R$^1$ is C$_1$–C$_5$ alkyl,
R$^3$ is hydrogen, C$_1$–C$_5$ alkyl, C$_1$–C$_5$ alkoxy or aryloxy, and R$^4$ is C$_1$–C$_5$ alkoxyl or aryloxy, with a aldehyde of formula R$^2$CHO, wherein R$^2$ is as defined above;

to obtain a compound of formula 6

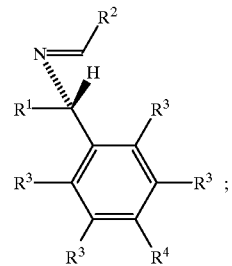

wherein R$^1$, R$^2$, R$^3$ and R$^4$ are as defined above, b) reaction of the compound of formula 6 with an acyl chloride R$^5$CO$_2$CH$_2$COCl of formula 7, wherein R$^5$ is as defined above, in the presence of triethylamine, to obtain a mixture of diastereo-isomeric β-lactams of the formulae 8a and 8b:

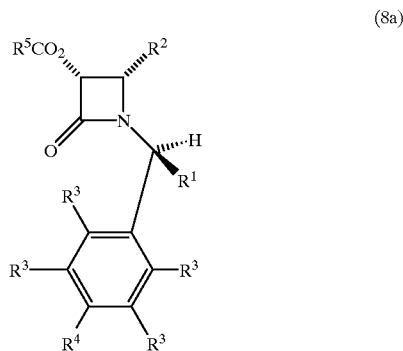

(8a)

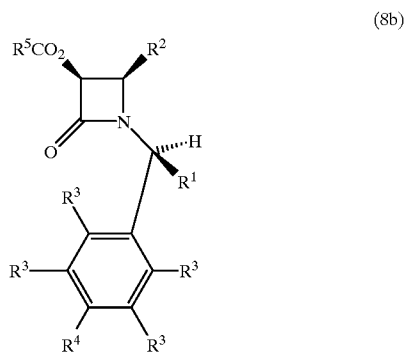

(8b)

wherein R$^1$, R$^2$, R$^3$, R$^4$ and R$^5$ are as defined above, and c) separation of the β-lactams of formulae 8a and 8b, to obtain an enantiomerically pure β-lactam of formula 8a, followed by treatment of said β-lactam of formula 8a with cerium ammoniumnitrate [Ce(NH$_4$)$_2$(NO$_3$)$_6$] in the presence of acetonitrile and water, to obtain the β-lactam having formula 9.

2. A process according to claim 1, wherein said β-lactams of formulae 8a and 8b are separated by recrystallisation from an ethyl acetate/hexane mixture.

3. A process according to claim 1, wherein step b) is effected in hexane, benzene or in DMF, preferably DMF, as reaction solvent.

4. A process according to claim 1, wherein compounds are used wherein:

$R^1$ is $C_1$–$C_5$ alkyl,
$R^2$ is aryl, substituted or not,
$R^3$ is hydrogen,
$R^4$ is $C_1$–$C_5$ alkoxyl or aryloxy, and
$R^5$ is $C_1$–$C_5$ alkyl.

5. Enantiomerically pure (S)-(−)-1-(p-methoxyphenyl)propyl-1-amine.

6. A process for the preparation of enantiomerically pure (S)-(−)-1-(p-methoxy-phenyl)propyl-1-amine from a racemic mixture of said amine, by resolution with an optically active amino acid, wherein a racemic mixture of 1-(p-methoxyphenyl)propyl-1-amine having formula (14) is reacted with N-acetyl-L-leucine having formula (15) to provide the diastereoisomeric salts having formula (16),

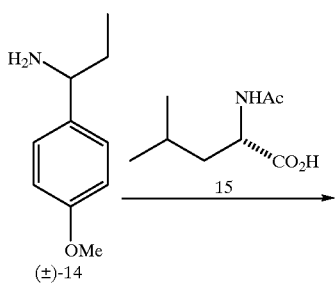

followed by fractional crystallisation from water to obtain the (S)-amine-N-acetyl-L-leucine salt having formula (16), which salt (16) is thereafter treated with sodium hydroxide to give the desired (S)-(−)-1-(p-methoxyphenyl)propyl-1-amine having formula (14) and N-acetyl-L-leucine, which may, if desired, be recycled:

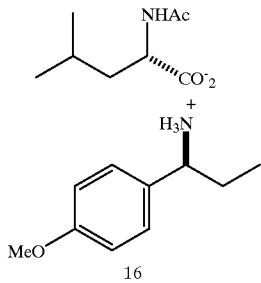

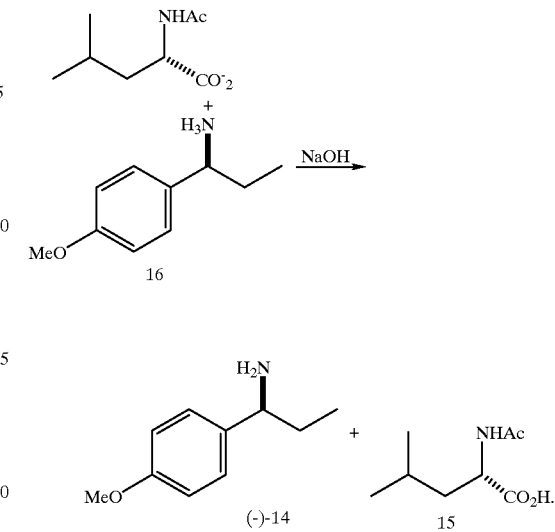

7. A process for the preparation of pactitaxel by reaction of 10-deacetylbaccatin III with a β-lactam,
    wherein a β-lactam of formula 9, obtained according to a process according to claim 1 is used.

8. A pharmaceutical composition containing paclitaxel, wherein said paclitaxel is obtained from a β-lactam prepared according to claim 7.

9. A process for preparation a beta-lactam according to claim 1 comprising reacting enantiomerically pure (S)-(−)-1-(p-methoxyphenyl)propyl-1-amine and acetoxyacetyl chloride to obtain the (−)-azetidinone of formula (13), wherein Ac represents the acetyl residue and Ph represents a phenyl group:

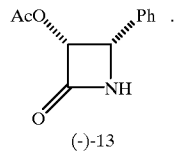

* * * * *